United States Patent [19]
Preston et al.

[11] Patent Number: 5,563,301
[45] Date of Patent: Oct. 8, 1996

[54] SEQUENTIAL REACTION OF TBA AND ISOBUTYLENE WITH METHANOL

[75] Inventors: Kyle L. Preston, Port Arthur; Lawrence E. Tillotson, Port Neches; Rei-Yu J. Hwan, Sugarland, all of Tex.

[73] Assignee: Texaco Development Corp., White Plains, N.Y.

[21] Appl. No.: 345,663

[22] Filed: Nov. 28, 1994

[51] Int. Cl.$^6$ .................................................. C07C 41/00
[52] U.S. Cl. ........................................... 568/698; 568/671
[58] Field of Search ..................................... 568/698, 671

[56] References Cited

U.S. PATENT DOCUMENTS

| | | | |
|---|---|---|---|
| 5,243,091 | 9/1993 | Kruse | 568/698 |
| 5,292,964 | 3/1994 | Gupta | 568/698 |
| 5,354,912 | 10/1994 | Hwan | 568/698 |
| 5,386,065 | 1/1995 | Kruse | 568/698 |
| 5,387,721 | 2/1995 | Kruse | 568/698 |
| 5,387,722 | 2/1995 | Knifton | 568/698 |
| 5,387,723 | 2/1995 | Knifton | 568/698 |
| 5,395,982 | 3/1995 | Cassata | 568/698 |

*Primary Examiner*—Paul J. Killos
*Attorney, Agent, or Firm*—James L. Bailey; Kenneth R. Priem; Cynthia L. Hunter

[57] ABSTRACT

Methyl tertiary butyl ether is sequentially prepared from tertiary butyl alcohol and methanol by:

passing tertiary butyl alcohol and methanol through a primary reaction zone to form a primary etherification reaction product comprising unreacted methanol, unreacted tertiary butyl alcohol, water, dimethyl ether, isobutylene and methyl tertiary butyl ether;

separating the primary etherification reaction product into a methanol recycle fraction, a tertiary butyl alcohol recycle fraction, an isobutylene fraction and a methyl tertiary butyl ether product fraction;

recycling the methanol recycle fraction and the tertiary butyl alcohol recycle fraction to the methyl tertiary butyl ether etherification reaction zone;

passing at least a portion of said isobutylene fraction together with added methanol through a secondary reaction zone to form a secondary etherification reaction product comprising water, methanol, isobutylene, DME, methyl tertiary butyl ether and tertiary butyl alcohol; and recovering the methyl tertiary butyl ether from said secondary etherification reaction product.

4 Claims, 1 Drawing Sheet

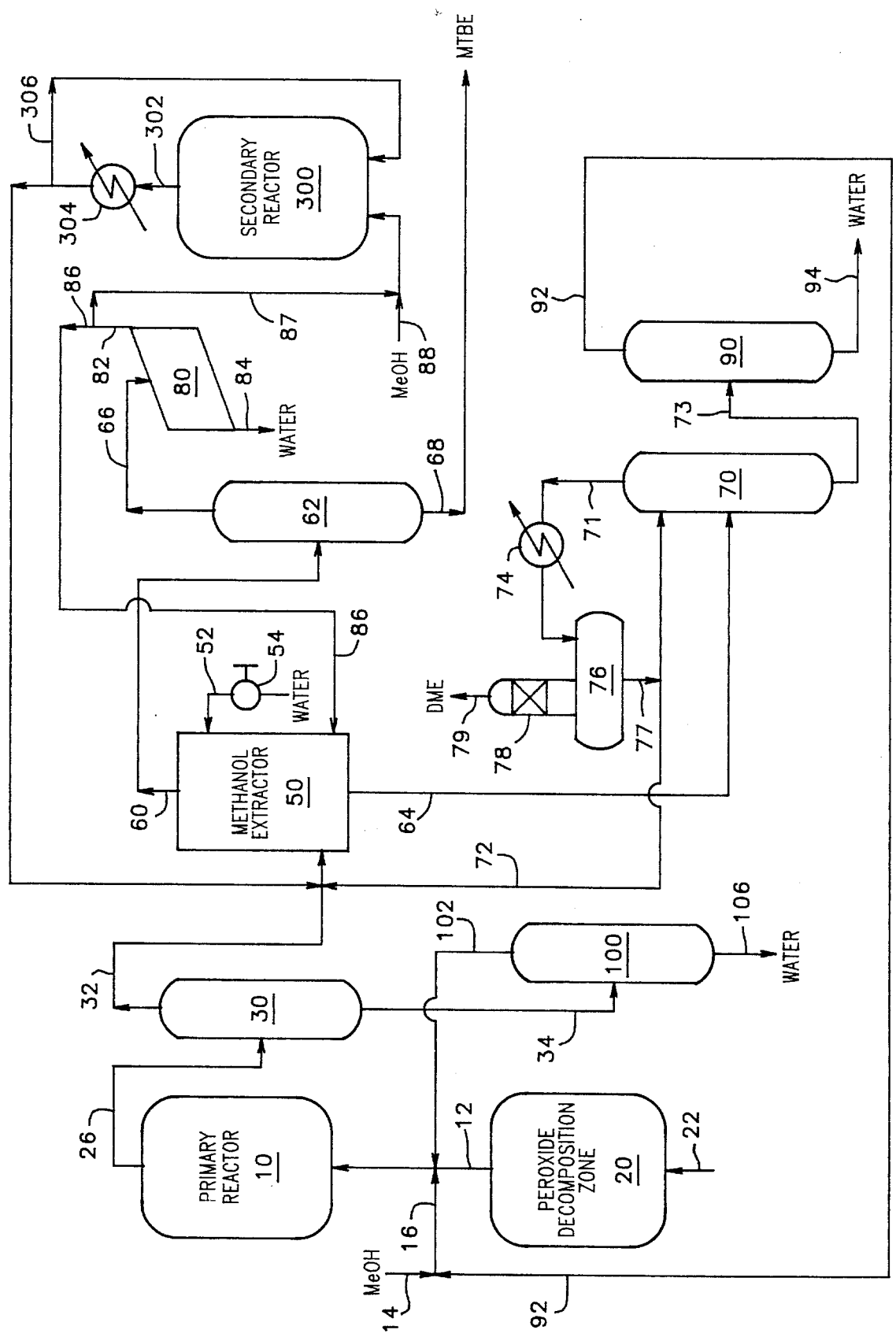

SEQUENTIAL REACTION OF TBA AND ISOBUTYLENE WITH METHANOL

BACKGROUND OF THE INVENTION

1. Technical Field of the Invention

This invention relates to a method for the manufacture of methyl tertiary butyl ether by the sequential reaction of tertiary butyl alcohol and isobutylene with methanol. More particularly, this invention relates to a method for the manufacture of methyl tertiary butyl ether by the sequential reaction of tertiary butyl alcohol and isobutylene with methanol and to the purification of the methyl tertiary butyl ether formed by the reactions.

2. Prior Art

In coassigned allowed application Ser. No. 08/969,482, filed Jun. 1, 1993 (D# 81,243) and entitled "METHOD FOR THE REMOVAL OF DIMETHYL ETHER FROM METHYL TERTIARY BUTYL ETHER" now U.S. Pat. No. 5,354,912; there is disclosed an improved method for the removal of dimethyl ether formed as a reaction by-product when tertiary butyl alcohol and isobutylene are reacted with methanol.

In coassigned application Ser. No. 08/147,508, filed Nov. 5, 1993 (D# 81,181) and entitled "CONTINUOUS ISOBUTYLENE ASSISTED AQUEOUS EXTRACTION OF METHANOL FROM METHYL TERTIARY BUTYL ETHER" now U.S. Pat. No. 5,395,982; there is disclosed a method for the continuous purification of methyl tertiary butyl ether contaminated with isobutylene, methanol and water, by the sequential steps of water extraction in the presence of an added isobutylene stripping agent to form an extract and a raffinate, distillation of the raffinate to form a heavier product methyl tertiary butyl ether fraction and a lighter isobutylene fraction from which isobutylene is recovered for recycle to the extraction zone.

Kruse et al. U.S. Pat. No. 5,243,091 discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol, isobutylene and water, wherein the reaction product is separated in a distillation zone into a lighter fraction comprising methanol, isobutylene and methyl tertiary butyl ether and a heavier fraction comprising tertiary butyl alcohol, methanol and water, and wherein the lighter fraction is charged to a finishing reactor wherein isobutylene and methanol are reacted to form additional methyl tertiary butyl ether.

Gupta U.S. Pat. No. 5,292,964 also discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lighter fraction comprising substantially anhydrous methanol and methyl tertiary butyl ether and a heavier fraction comprising tertiary butyl alcohol, methanol and water, and wherein the lighter fraction is charged to a finishing reactor wherein the methanol is reacted with isobutylene to form additional methyl tertiary butyl ether.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

BACKGROUND INFORMATION

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol catalyzed by a cationic ion-exchange resin.

With the expanding use of MTBE as an acceptable gasoline additive, a growing problem is the availability of raw materials. Historically, the critical raw material is isobutylene (Oil and Gas J., Jun. 8, 1987, P. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

It is known to react methanol with tertiary butyl alcohol in the presence of a catalyst in order to product methyl tertiary butyl ether. A wide variety of catalysts have been suggested for this purpose.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

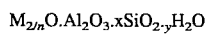

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

Two of the principal by-products formed during the reaction of the methanol with the tertiary butyl alcohol are water and isobutylene. The separation of MTBE from methanol during the recovery of purified MTBE presents a serious problem.

In U.S. Pat. No. 4,820,877, separation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of crosslinked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to forman azeotrope with methanol. This azeotrope is recovered overhead giving a methanol-free MTBE bottoms product.

As recognized by Rao et al. in U.S. Pat. No. 4,144,138, isobutylene is formed as a by-product when methanol is reacted with tertiary butyl alcohol. In accordance with the Rao process, the isobutylene is separated from the reaction product in an initial azeotropic distillation step as a noncondensable gas. Rao teach that part of the isobutylene may be flashed from the reaction product for recycle, depending upon purity.

SUMMARY OF THE INVENTION

The present invention is directed to a process for the preparation of methyl tertiary butyl ether by the sequential reaction of tertiary butyl alcohol and isobutylene with methanol and to the purification of the methyl tertiary butyl ether formed by the reactions, whereby a methyl tertiary butyl ether product of improved purity is obtained, the methyl tertiary butyl ether product being characterized by very low levels of water, methanol and tertiary butyl alcohol contamination.

More particularly, the present invention is directed to a method for the continuous preparation of methyl tertiary butyl ether (MTBE) from tertiary butyl alcohol (TBA), isobutylene (IBTE) and methanol (MeOH), which comprises the steps of:

a) continuously passing a feed mixture comprising tertiary butyl alcohol and methanol through a methyl tertiary butyl ether etherification reaction zone containing a bed of a TBA/MeOH etherification catalyst under etherification reaction conditions to form a primary etherification reaction product comprising unreacted methanol, unreacted tertiary butyl alcohol, water, isobutylene and methyl tertiary butyl ether;

b) continuously separating said primary etherification reaction product into a methanol recycle fraction, a tertiary butyl alcohol recycle fraction, an isobutylene fraction and a methyl tertiary butyl ether product fraction;

c) continuously recycling said methanol recycle fraction and said tertiary butyl alcohol recycle fraction to the methyl tertiary butyl ether etherification reaction zone;

d) continuously passing at least a portion of said isobutylene fraction together with added methanol through an isobutylene etherification reaction zone containing a bed of a isobutylene/methanol etherification catalyst under etherification reaction conditions to form a secondary etherification reaction product comprising water, methanol, isobutylene, methyl tertiary butyl ether and tertiary butyl alcohol; and e) continuously recovering the methyl tertiary butyl ether from said secondary etherification reaction product.

A preferred embodiment of the present invention comprises the steps of:

a) charging a mixture of methanol and tertiary butyl alcohol in the molar ratio of about 0.5 to 4 moles of methanol per mol of tertiary butyl alcohol to an etherification reaction zone containing a bed of an etherification catalyst under reaction conditions including a pressure of about 30 to about 500 psia, a temperature of abut 80° to about 140° C. and a flow rate of about 0.5 to about 20 volumes of feed mixture per volume of etherification catalyst per hour to thereby form a reaction product comprising unreacted methanol, unreacted tertiary butyl alcohol, water, dimethyl ether, isobutylene and methyl tertiary butyl ether;

b. charging the reaction product to a first methyl tertiary butyl ether recovery distillation zone and separating it therein into a first lighter distillation fraction comprising isobutylene, dimethyl ether, methanol, water and methyl tertiary butyl ether and a second heavier distillation fraction comprising methanol, tertiary butyl alcohol and water;

c. charging the first lighter distillation fraction to a methanol solvent extraction zone and counter-currently contacting the reaction product therein with water in the ratio of about 1 to about 10 volumes of the first lighter distillation fraction per volume of water per hour under extraction conditions including a temperature of about 20° to about 60° C. and a pressure of about 50 to about 500 psia to thereby provide an overhead raffinate comprising isobutylene, dimethyl ether (DME), water and methyl tertiary butyl ether and an extract comprising methanol, MTBE, DME and water;

d. charging the raffinate to a second methyl tertiary butyl ether purification distillation zone and separating it therein into a third lighter distillation fraction comprising isobutylene, DME and water and a fourth heavier distillation fraction consisting essentially of substantially anhydrous methyl tertiary butyl ether substantially free from tertiary butyl alcohol;

e. charging the third distillation fraction to a decantation separation zone and separating it therein into an isobutylene DME fraction and a water fraction;

f. continuously charging at least a portion of the isobutylene DME fraction and added methanol to an isobutylene conversion reaction zone in the molar ratio of about 0.2 to about 4 moles of methanol per mol of isobutylene and contacting them therein with a solid resin etherification catalyst under conversion conditions including a temperature of about 20° to about 130° C., a pressure of about 50 to about 500 psia and a flow rate of about 0.5 to about 4 volumes of isobutylene fraction per volume of solid resin etherification catalyst per hour to thereby convert a portion of the isobutylene and a portion of the methanol to methyl tertiary butyl ether and form an isobutylene conversion product comprising methyl tertiary butyl ether, unreacted isobutylene, DME, unreacted methanol, tertiary butyl alcohol and water;

g. continuously charging the extract to a third methyl tertiary butyl ether distillation zone and separating it therein into a fifth lighter azeotrope distillation fraction comprising methyl tertiary butyl ether, DME and isobutylene and a sixth heavier distillation fraction comprising methanol and water;

h. charging the sixth distillation fraction to a fourth methanol recovery distillation zone and separating it therein into a seventh lighter distillation fraction comprising methanol and an eighth heavier distillation fraction comprising water; and i. charging the second distillation fraction to a fifth tertiary butyl alcohol recovery distillation zone and separating it therein into a ninth lighter distillation fraction comprising methanol, tertiary butyl alcohol and water and a tenth heavier distillation fraction comprising a water fraction.

The isobutylene conversion product and the fifth lighter MTBE fraction may be recycled to the methanol solvent extraction zone. The seventh lighter methanol fraction and the ninth lighter tertiary butyl alcohol fraction may be recycled to the methyl tertiary butyl ether etherification reaction zone.

Tertiary butyl alcohol is frequently produced by the thermal or catalytic decomposition of tertiary butyl hydroperoxide. Tertiary butyl alcohol formed in this fashion will normally contain a minor amount of peroxide contaminants such as tertiary butyl hydroperoxide, ditertiary butyl peroxide, allyl tertiary butyl peroxide, etc. Normally, the peroxide contaminants in the tertiary butyl alcohol will remain as contaminants in the etherification reaction zone reaction product. Preferably, therefore, the tertiary butyl alcohol feedstock is charged to a suitable peroxides decomposition zone, such as a thermal peroxides decomposition zone, where the peroxide contaminants are thermally decomposed under decomposition conversion conditions including a temperature of about 100° to about 200° C., a pressure of about 80 to about 500 psia and a flow rate of about 0.5 to about 4 volumes of tertiary butyl alcohol per volume of said solid peroxide decomposition catalyst per hour to thereby decompose the peroxide contaminants and form a tertiary butyl alcohol effluent substantially completely free from peroxide contaminants.

DETAILED DESCRIPTION OF THE PRESENT INVENTION

The Etherification Reaction Catalyst

In accordance with the MTBE manufacture and purification method of the present invention, an etherification reaction zone containing a bed of etherification catalyst is utilized. A wide variety of etherification catalysts can be used for this purpose. For example, a solid resin etherification catalyst may be used for this purpose, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138. A solid acidic catalyst may be used, such as Kieselguhr impregnated with a phosphoric acid as disclosed in Frolich U.S. Pat. No. 2,282,469, zeolites as disclosed in Japanese Patent 0007432, aluminosilicate zeolites as disclosed in Chang et al. U.S. Pat. No. 4,058,576, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc.

The reaction conditions to be utilized when reacting methanol with tertiary butyl alcohol in the presence of an etherification catalyst of the type disclosed in the prior art include a reaction temperature of about 90° to about 140° C., a pressure of about 30 to about 500 psia and a flow rate of about 0.5 to about 20 volumes of feed per volume of etherification catalyst per hour.

The Solid Resin Etherification Catalyst

In accordance with the present invention, methyl tertiary butyl ether and isobutylene are separately recovered from the primary reaction product and the recovered isobutylene and methanol are brought into contact with a solid resin etherification catalyst in order to convert a significant portion of the isobutylene and methanol to methyl tertiary butyl ether.

Any suitable solid resin etherification catalyst may be used for this purpose, such as a strongly acidic ion exchange resin consisting essentially of sulfonated polystyrene, such a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

The isobutylene and methanol are brought into contact with a solid resin etherification catalyst in an isobutylene conversion reaction zone under conversion conditions including, for example, a temperature of about 20° to about 130° C., a pressure of about 50 to about 500 psia and a flow rate of about 1 to about 10 volumes of isobutylene/methanol feed per volume of etherification catalyst per hour.

The Peroxidation Decomposition Catalyst

In accordance with one embodiment of the present invention, the tertiary butyl alcohol feedstock is charged to a peroxidation decomposition reaction zone and may be contacted therein with a solid peroxide decomposition catalyst.

A wide variety of catalysts may be used for this purpose, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The conversion conditions to be utilized in the peroxide decomposition zone may comprise, for example, a temperature of about 100° to about 200° C., a pressure of about 80 to about 500 psia and a flow rate of about 0.5 to about 20 volumes of feed per volume of catalyst per hour.

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary etherification reaction zone 10 containing a bed of a solid etherification catalyst, such as a solid resin etherification catalyst (e.g., a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138). As another example, the catalyst may comprise fluorophosphoric acid-on-titania catalyst prepared in the manner described in Knifton et al. U.S. Pat. No. 4,822,921 by treating titania extrudates such as extrudates having a surface area of about 50 $m^2/g$ with an acetone solution of fluorophosphoric acid to provide as a catalyst, titania having about 3.0 wt. % of phosphorus and about 0.6 wt. % of fluorine deposited thereon and bonded thereto by a calcining treatment.

A feed mixture is charged to the etherification reaction zone 10 by way of a line 12.

When the tertiary butyl alcohol is prepared by the thermal or catalytic decomposition of tertiary butylhydroperoxide, it will contain minor amounts of impurities such that, for example, the feedstock charged to the reactor 10 will contain the following components:

| ETHERIFICATION REACTION ZONE FEED MIXTURE | |
| --- | --- |
| Component | wt. % (approximate) |
| Methanol | 41.0 |
| TBA[1] | 47.0 |
| Acetone | 0.5 |
| 2-Propanol | 6.0 |
| MTBE[2] | 0.2 |
| DTBP[3] | 0.1 |
| t-Butyl Formate | 0.1 |
| Water | 6.0 |

[1]Tertiary butyl alcohol
[2]Methyl tertiary butyl ether
[3]Ditertiary butyl peroxide The peroxides decomposition reactor 20 may be operated, for example, as a thermal peroxides decomposition reactor and operated (e.g.) at a temperature of about 100° to about 200° C., a pressure of about 80 to about 500 psia and a flow rate of about 0.5 to 20 volumes of feedstock per reactor volume per hour to thereby provide a substantially peroxide-free tertiary butyl alcohol reaction product. The peroxide contaminants will be decomposed to form water, methanol and tertiary butyl alcohol, and trace amounts of other decomposition products such as acetone and methyl formate.

The substantially peroxide-free tertiary butyl alcohol reaction product is continuously discharged from the peroxides decomposition reactor 20 by line 12 leading to the etherification reaction zone 10. Methanol is charged to the line 12 by a line 16. The flow of methanol and tertiary butyl alcohol to the etherification reaction zone 10 is regulated so that a molar excess of methanol is present such as, for example, a molar ratio of about 1.1 to about 3 moles of methanol per mol of tertiary butyl alcohol.

Within the etherification reaction zone 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., a still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will exothermically react with the tertiary butyl alcohol to form methyl tertiary butyl ether which will be contained in a reaction product discharged from the etherification reaction zone 10 by way of a line 20 leading to a first methyl tertiary butyl ether (MTBE) distillation zone 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 is within the ratio of about 2.0 moles of methanol per mole of tertiary butyl alcohol, and the reaction is conducted at a temperature of about 100° C. at a feed rate of about 2.0 volumes of feed mixture per volume of catalyst per hour, the etherification reaction product may have the composition in part shown by the following table:

| ETHERIFICATION REACTION PRODUCT | |
| --- | --- |
| Component | wt. % |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, ditertiary butyl peroxide, tertiary butyl formate, etc., initially present in the tertiary butyl alcohol feedstock and DME (formed from methanol).

The etherification reaction product charged to the first MTBE distillation zone 30 by way of the charge line 26 is fractionated therein under distillation conditions including a liquid reflux temperature of about 25° to about 100° C., and more preferably about 30° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reactor 10 is taken overhead from the first distillation zone 30 by a line 32 and such that substantially all of the tertiary butyl alcohol exits the column 30 through the line 34. As a consequence, the first distillation fraction 32 taken overhead from the distillation zone 30 will comprise substantially all of the isobutylene, methyl tertiary butyl ether and DME and some of the methanol and water charged to the first distillation zone 30. The second heavier distillation fraction 34 discharged from the first. distillation zone 30 will comprise methanol, tertiary butyl alcohol and water.

In accordance with the present invention, the first distillation fraction 32 and recycle fractions 72 and 310 are charged to a solvent extraction tower 50. As explained in greater detail hereafter, the recycle fraction 72 contains methyl tertiary butyl ether, DME, methanol and isobutylene and the recycle fraction 310 contains isobutylene, DME and trace amounts of water and methanol. Within the solvent extraction tower 50 the hydrocarbon streams 32, 72 and 310 are counter-currently contacted with water introduced by a water charge line 52 controlled by a valve 54 so that methanol can be extracted from the other hydrocarbons with water to thereby form an aqueous extract phase and a hydrocarbon raffinate phase. The efficiency of the extraction is improved by the isobutylene present in the extraction tower.

Within the methanol extraction tower 50, solvent extraction conditions are established for countercurrent solvent extraction including a ratio of hydrocarbon feed to water within the range of about 0.8 to 1.8 volumes of hydrocarbon per volume of water per hour, and more preferably, a ratio of about 1.0 to about 1.5 volumes of hydrocarbon per volume of water. Extraction conditions to be established may suitably include a temperature of about 20° to about 60° C., and more preferably, from about 30° to about 40° C., and a pressure of about 50 to 500 psia, and more preferably from about 50 to 150 psia.

As a consequence, a supernatant raffinate will be formed which is withdrawn from the top of the methanol solvent extraction tower 50 by line 60. The extract is discharged from the solvent extraction tower 50 by way of a bottoms charge line 64 leading to a third methyl tertiary butyl ether distillation zone 70.

Within the second methyl tertiary butyl ether purification distillation zone 62, distillation conditions are established including a liquid reflux temperature of about 30° to about 60° C., and more preferably from about 40° to about 55° C., a reboiler temperature of about 100° to about 140° C. and more preferably from about 125° to about 135° C. and a pressure of about 70 to about 120 psia, and more preferably from about 90 to about 110 psia, to thereby form a lighter distillation fraction 66 discharged from the second distillation zone 62 and a heavier fourth distillation fraction 68 consisting essentially of product, namely substantially anhydrous methyl tertiary butyl ether substantially free from tertiary butyl alcohol.

The third distillation fraction 66 will comprise a mixture of isobutylene, DME and water and suitably may be charged to a decantation zone 80 where it can settle to form a supernatant isobutylene/DME phase withdrawn by way of a line 82 and a water phase withdrawn by way of a water discharge line 84 and suitably purged from the system. A portion of the isobutylene in the line 82 is recycled by way of line 86 to the methanol solvent extraction zone 50.

In accordance with the present invention, the isobutylene recovered from the decanter is reacted with methanol in a secondary reactor to form additional methyl tertiary butyl ether. The reaction of isobutylene with methanol is exothermic and it is necessary to provide for positive control of the reaction temperature. This is accomplished in accordance with the present invention by limiting the rate at which isobutylene is charged to the secondary reactor and by diluting the charged isobutylene with a stream of cooled recycled reaction product.

Thus, about 80 to 95 wt. % of the isobutylene discharged from the decanter 80 is recycled by line 86 to methanol extractor 50 to facilitate the removal of methanol from methyl tertiary butyl ether as disclosed in application Ser. No. 08/147,508 entitled "Continuous Isobutylene Assisted Extraction of Methanol from Methyl Tertiary Butyl Ether" now U.S. Pat. No. 5,395,982.

The remaining 10 to 15 wt. % of the isobutylene in line 82 is charged through line 87 to the secondary reactor 300 together with methanol charged by the line 88. The methanol should be mixed with the isobutylene in the line 87 in an amount sufficient to provide for a molar ratio of about 0.5 to about 3 moles of methanol per mol of isobutylene. The secondary reactor 300 may suitably contain a fixed bed of a suitable isobutylene/methanol etherification catalyst, such as a bed of Amberlyst 15 sulfonated polystyrene-divinyl benzene copolymer acidic ion exchange resin.

Etherification reaction conditions established in the secondary reaction zone may include, for example, a temperature of about 20° to about 160° C., and more preferably from about 35° to about 100° C., a pressure of about 50 to 500 psia, and more preferably from about 150 to 250 psia, and a flow rate of about 0.5 to 10 volumes of feed per volume of solid resin etherification catalyst per hour. As a consequence, a portion of the methanol and isobutylene contained in the feed will be converted to methyl tertiary butyl ether. Typically, the conversion will amount to about 30 to 98 wt. %, based on the isobutylene in stream 87.

As a consequence, there will be formed an isobutylene conversion product discharged from the secondary reactor by a line 302 leading to heat exchanger 304 where the reaction product is cooled to a temperature of about 30° to about 100° C. About 10 to 20 mol % of the reaction product is recycled by the line 310 to the methanol extractor 50. The remainder of the reaction product is recycled to the secondary reactor by the line 306 as a diluent. The composition of a typical isobutylene conversion product may be characterized as follows:

| ISOBUTYLENE CONVERSION PRODUCT | |
| --- | --- |
| Component | wt. % |
| Isobutylene | 8.4 |
| MTBE | 73.3 |
| Methanol | 3.0 |
| Tertiary Butyl Alcohol | 0.8 |
| Dimethyl Ether | 14.3 |
| Water | 0.02 |
| Other | 2.9 |

The extract 64 charged to the third distillation zone 70 will comprise methyl tertiary butyl ether, isobutylene, dimethyl ether, methanol and water, and is suitably fractionated therein under distillation conditions including a liquid reflux temperature of about 20° to about 90° C., and more preferably from about 30° to about 60° C., and a reboiler temperature of about 80° to about 120° C., and more preferably from about 105° to about 115° C., and a pressure of about 15 to about 60 psia, and more preferably from about 40 to about 50 psia, to form a fifth lighter distillation fraction 71 comprising methyl tertiary butyl ether, dimethyl ether, etc., which may suitably be partially liquified in heat exchanger 74 and then charged to surge drum 76 from which the dimethyl ether may be removed by line 79 leading from condenser/fractionator 78. The removal of the dimethyl ether is disclosed and described in greater detail in copending application Ser. No. 08/969,482, filed Jun. 1, 1993, and entitled "Method for the Removal of Dimethyl Ether from Methyl Tertiary Butyl Ether". The remaining overhead product, mostly methyl tertiary butyl ether is recycled by the line 72 to methanol extractor 50 for ultimate recovery as product.

A sixth heavier distillation fraction comprising water and methanol is discharged from the third distillation zone 70 by a line 73 leading to a fourth distillation zone 90. The sixth distillation fraction charged to the fourth methanol distillation zone 90 is fractionated therein under distillation conditions which may suitably include a liquid reflux temperature of about 20° to about 80° C., and more preferably from about 30° to about 60° C., a reboiler temperature of about 100° to about 140° C., and more preferably from about 110° to about 120° C., and a pressure of about 15 to about 60 psia, and more preferably from about 20 to about 30 psia, into a seventh lighter distillation fraction 92 which suitably may be recycled to the methanol charge line 16. A heavier distillation fraction consisting essentially of water is discharged from the fourth methanol distillation zone by way of a line 94 and may be discharged from the system or recycled by a line (not shown) leading to the water charge line 52 for the extraction tower 50.

The second distillation fraction 34 discharged from the first MTBE distillation zone 30 is charged to a fifth tertiary butyl alcohol recovery distillation zone 100 where it is fractionated under distillation conditions including a liquid reflux temperature of about 80° to about 170° C., and more preferably about 100° to about 150° C., and a reboiler temperature of about 100° to about 190° C., more preferably about 170° to about 180° C., and at a pressure of about 15 to about 190 psia, and more preferably about 110 to about 160 psia, into a ninth distillation fraction comprising mostly tertiary butyl alcohol and methanol that is discharged in the fifth distillation zone 100 by a line 102 leading to the charge line 12 for the primary reactor 10. A tenth heavier distillation fraction comprising a third water fraction is discharged from the distillation zone 100 by a line 106.

Having thus described our invention, what is claimed is:

1. A method comprising the steps of:

(a) charging a mixture of methanol and tertiary butyl alcohol to an etherification zone containing a bed of an etherification catalyst under etherification reaction conditions to form a reaction product comprising unreacted methanol, unreacted tertiary; butyl alcohol, water, isobutylene, DME and methyl tertiary butyl ether;

(b) charging the reaction product to a first methyl tertiary butyl ether recovery distillation zone and separating it therein into a first lighter distillation fraction comprising isobutylene, DME, methanol, water and methyl tertiary butyl ether and a second heavier distillation fraction comprising methanol, tertiary butyl alcohol and water;

(c) charging the first lighter distillation fraction to a methanol solvent extraction zone and countercurrently contacting the first lighter distillation fraction therein with water to provide an overhead raffinarte comprising isobutylene, DME, water and methyl tertiary butyl ether, and an extract comprising methanol, MTBE, isobutylene, dimethyl ether and water;

(d) charging the raffinate to a second methyl tertiary butyl ether purification distillation zone and separating it therein into a third lighter distillation fraction comprising isobutylene, DME and water and a fourth heavier distillation fraction consisting essentially of substantially anhydrous methyl tertiary butyl ether substantially free from tertiary butyl alcohol;

(e) recovering an isobutylene fraction from the third distillation fraction, (f) charging at least a portion of the recovered isobutylene and added methanol to an isobutylene conversion zone containing a solid resin etherification catalyst to convert a portion of the isobutylene and a portion of the methanol to methyl tertiary butyl ether and to form an isobutylene conversion product comprising methyl tertiary butyl ether, unreacted isobutylene, unreacted methanol, DME, tertiary butyl alcohol and water;

(g) charging the extract to a third methyl tertiary butyl ether distillation zone and separating it therein into a fifth lighter distillation fraction comprising methyl tertiary butyl ether, methanol, isobutylene, and dimethyl ether and a sixth heavier distillation fraction comprising methanol and water;

(h) charging the sixth distillation fraction to a fourth methanol recovery distillation zone and separating it therein into a seventh lighter distillation fraction comprising methanol and an eighth heavier distillation fraction comprising water; and (i) charging the second distillation fraction to a fifth tertiary butyl alcohol recovery distillation zone and separating it therein into a ninth lighter distillation fraction comprising methanol, tertiary butyl alcohol and water and a tenth heavier distillation water fraction.

2. A method comprising the steps of:

a. charging a mixture of methanol and tertiary butyl alcohol in the molar ratio of about 0.7 to 4 moles of methanol per mole of tertiary butyl alcohol to an etherification reaction zone containing a bed of an etherification catalyst under reaction conditions including a pressure of about 30 to about 500 psia, a temperature of about 90° to about 140° C. and a flow rate of about 0.5 to about 20 volumes of feed mixture per volume of etherification catalyst per hour to thereby form a reaction product comprising unreacted methanol, unreacted tertiary butyl alcohol, water, isobutylene, DME and methyl tertiary butyl ether;

b. charging the reaction product to a first methyl tertiary butyl ether recovery distillation zone and separating it therein into a first lighter distillation fraction comprising isobutylene, DME, methanol, water and methyl tertiary butyl ether and a second heavier distillation fraction comprising methanol, tertiary butyl alcohol and water;

c. charging the first lighter distillation fraction to a methanol solvent extraction zone and counter-currently contacting the first lighter distillation fraction therein with water in the ratio of about 1 to about 10 volumes of the first lighter distillation fraction per volume of water per hour under extraction conditions including a temperature of about 20° to about 60° C. and a pressure of about 50 to about 500 psia to thereby provide an overhead raffinate comprising isobutylene, DME, water and methyl tertiary butyl ether and an extract comprising methanol, MTBE, isobutylene, dimethyl ether and water;

d. charging the raffinate to a second methyl tertiary butyl ether purification distillation zone and separating it therein into a third lighter distillation fraction comprising isobutylene, DME and water and a fourth heavier distillation fraction consisting essentially of substantially anhydrous methyl tertiary butyl ether substantially free from tertiary butyl alcohol;

e. charging the third distillation fraction to a decantation separation zone and separating it therein into an isobutylene fraction and a water fraction;

f. continuously charging at least a portion of the isobutylene fraction and added methanol to an isobutylene conversion reaction zone in the molar ratio of about 0.5 to about 4 moles of methanol per mol of isobutylene and contacting them therein with a solid resin etherification catalyst under conversion conditions including a temperature of about 20° to about 130° C. a pressure of about 50 to about 500 psia and a flow rate of about 0.5 to about 10 volumes of total reactor feed per volume of solid resin etherification catalyst per hour to thereby convert a portion of the isobutylene and a portion of the methanol to methyl tertiary butyl ether and form an isobutylene conversion product comprising methyl tertiary butyl ether, unreacted isobutylene, unreacted methanol, DME, tertiary butyl alcohol and water;

g. continuously charging the extract to a third methyl tertiary butyl ether distillation zone and separating it therein into a fifth lighter distillation fraction comprising methyl tertiary butyl ether, methanol, isobutylene and dimethyl ether and a sixth heavier distillation fraction comprising methanol and water;

h. charging the sixth distillation fraction to a fourth methanol recovery distillation zone and separating it therein into a seventh lighter distillation fraction comprising methanol and an eighth heavier distillation fraction comprising water; and i. charging the second distillation fraction to a fifth tertiary butyl alcohol recovery distillation zone and separating it therein into a ninth lighter distillation fraction comprising methanol, tertiary butyl alcohol and water and a tenth heavier distillation fraction comprising water.

3. A method as in claim 2 wherein the isobutylene conversion product and the fifth lighter MTBE fraction are recycled to the methanol solvent extraction zone.

4. A method as in claim 2 wherein the seventh lighter methanol fraction and the ninth lighter tertiary butyl alcohol fraction are recycled to the methyl tertiary butyl ether etherification reaction zone.

* * * * *